United States Patent [19]

Linton et al.

[11] Patent Number: 5,053,538
[45] Date of Patent: Oct. 1, 1991

[54] PROCESS FOR ENHANCED UREA PRODUCTION

[75] Inventors: Max Linton, Beaumaris; Anthony M. Brown, Mt. Gravatt, both of Australia

[73] Assignee: Austral-Pacific Fertilizers Ltd., Australia

[21] Appl. No.: 473,956
[22] PCT Filed: Aug. 12, 1988
[86] PCT No.: PCT/AU88/00301
    § 371 Date: Apr. 12, 1990
    § 102(e) Date: Apr. 12, 1990
[87] PCT Pub. No.: WO89/01468
    PCT Pub. Date: Feb. 23, 1989

[30] Foreign Application Priority Data

Aug. 13, 1987 [AU] Australia ............... PI3711

[51] Int. Cl.[5] ........................... C07C 273/04
[52] U.S. Cl. ........................ 564/70; 564/67; 564/65
[58] Field of Search ................. 564/65, 67, 70

[56] References Cited

U.S. PATENT DOCUMENTS

| 3,236,888 | 2/1966 | Wentworth | 564/65 |
| 4,231,961 | 11/1980 | Konoki et al. | 564/65 |
| 4,331,839 | 11/1980 | Barron et al. | 564/65 |
| 4,540,813 | 9/1985 | van Nassau et al. | 564/70 |
| 4,670,588 | 6/1987 | Zardi | 564/70 |

FOREIGN PATENT DOCUMENTS

| 1576811 | 8/1969 | France | 564/70 |
| 1440624 | 6/1976 | United Kingdom | 564/65 |
| 2083472 | 3/1982 | United Kingdom | 564/70 |

OTHER PUBLICATIONS

Ruf et al., "Simulation of Urea Dehydration Using Membranes", C.A. 101, 213027e (1984).
Ruf et al., "Simulation of Urea Plant, Enhancement of the Yield with New Tech.", CA 106, 155427a (1987).

Primary Examiner—Glennon H. Hollrah
Assistant Examiner—Susan P. Treaner
Attorney, Agent, or Firm—Sughrue, Mion, Zinn, Macpeak & Seas

[57] ABSTRACT

A process for the production of urea comprising the steps of reacting carbon dioxide and ammonia to form ammonium carbamate and subsequent decomposition of ammonium carbamate to form a reaction mixture comprising urea and water, wherein the reaction mixture is contacted with one side of a semi-permeable membrane, and a drying fluid capable of removing water and possibly other reaction products(s) from the reaction mixture is contacted with the other side of the semi-permeable membrane.

15 Claims, 2 Drawing Sheets

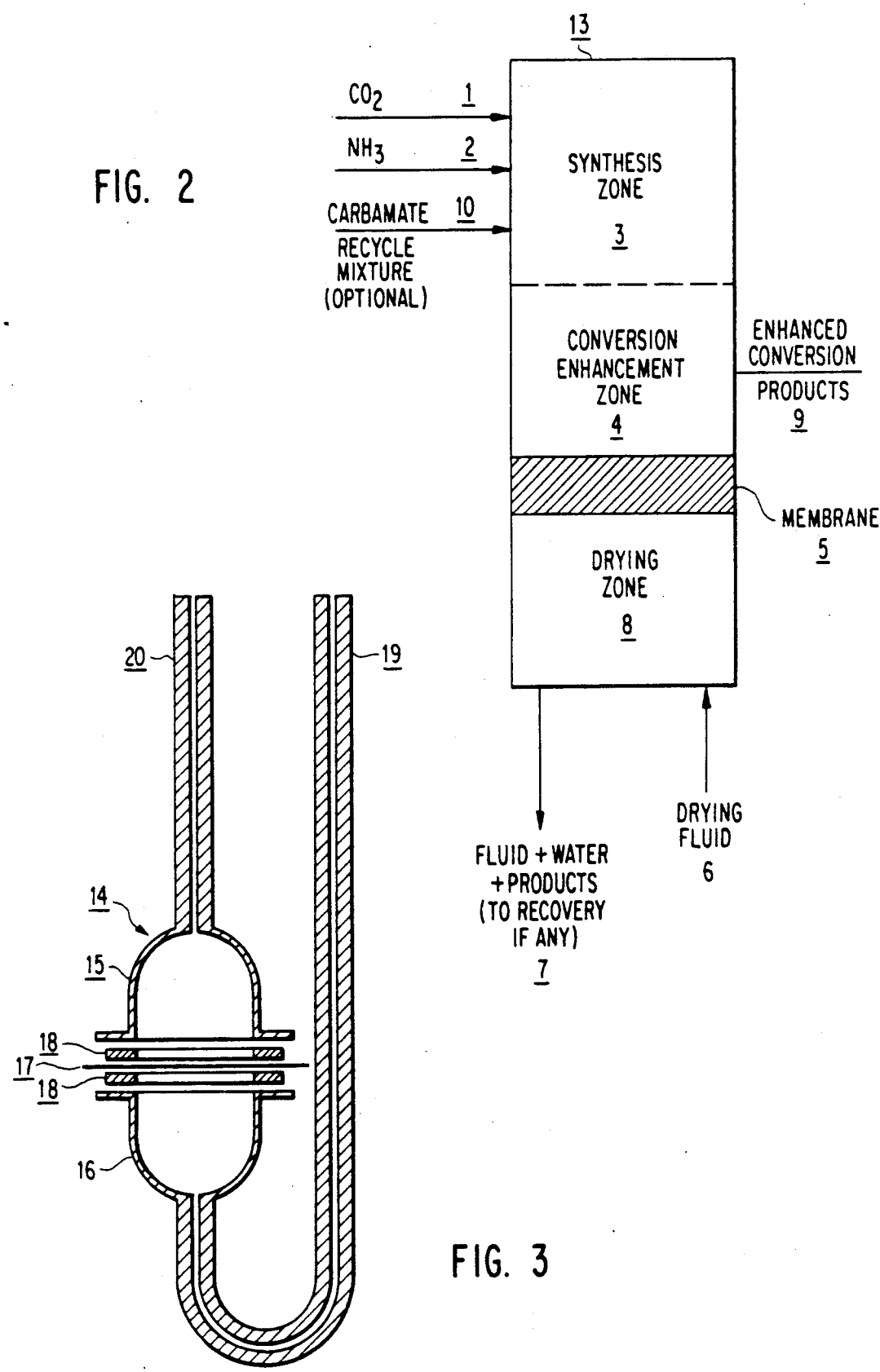

PROCESS FOR ENHANCED UREA PRODUCTION

This invention relates to an improved process for enhanced conversion and/or enhanced rates of conversion in the production of urea by reaction of carbon dioxide and ammonia.

BACKGROUND OF THE INVENTION

As is well known, carbon dioxide and ammonia can be caused to react with each other to form ammonium carbamate. It is also known that ammonium carbamate can be converted into urea and water. Moreover, urea can be produced directly from carbon dioxide and ammonia by causing the reaction to take place at a suitable temperature and pressure and for a sufficient period of time to allow the initially formed ammonium carbamate to be converted to urea. Typically, temperatures greater than 150° C. and pressures greater than 10MPa are used. This direct process is the basis for most commercial synthesis of urea at the present time. It is, however, also known that at any commercially practical suitable temperature and pressure, the percentage conversion, (which is the proportion of carbon dioxide fed to the process which is converted to urea, expressed as a percentage) is limited. It is further known that this limit is essentially due to an equilibrium being established as a result of the reverse reaction between water and urea. According to the most recent correlation in the literature (D. M. Gorlovskii and V. I. Kucheryavyi, Zhurnal Prikladnoi Khimii 53.11, 2548-2551 November 1980) the maximum possible conversion to urea at equilibrium is close to 86 percent, however the highest experimentally observed conversion to urea is close to 84 percent. Several of the most recent urea processes have been described by I. Mavrovic and A. R. Shirley in an article (Kirk-Othmer Encyclopedia of Chemical Technology, Third Edition, Published by John Wiley & Sons New York (1983) Vo. 23, p. 548-575), which indicates that in the present state of art, the highest conversion of carbamate to urea in a single pass is achieved by the UTI Heat-Recycle Process, with a reported 72-74 percent conversion per pass. In U.S. Pat. No. 3,236,888 (Wentworth) the only example cited gives the conversion to urea based on carbon dioxide introduced to the reactor as about 76 percent per pass. E. Guccione, (Chemical Engineering, Sept. 26, 1966 p. 96-98), in discussing this same process claims that the higher temperatures (380° to 450° F.) permit high conversion of $CO_2$ to urea of 80 to 85 percent.

It is also known from the literature (see Krase and Gaddy, Journal American Chemical Society 52, 3088-3093 (1930)) that attempts have been made to remove water produced by the above described process by using dehydrating agents, in either the gas or liquid phase, to increase the conversion of carbamate to urea.

In Ruf et al., (Swiss Chem 6 (1984) Nr. 9, 129-141 and Swiss Chem 8 (1986) Nr. 10a, 18-25) there is a theoretical description relating to simulation of a urea plant and enhancement of the yield based on a hypothetical new technology in which a semipermeable membrane selectively removes water from urea melts. It is stated in the latter paper that a reverse osmosis process is visualized in which the water is removed, across the membrane which forms the wall of the reactor, by means of the high pressure in the reactor and which overcomes the osmotic pressure gradient.

The paper states that no membrane is known to the authors which is capable of carrying out the process, but the future development of such is forseeable. It is further stated that the simulation, and computationally demonstrated benefits and improved methods of operation theoretically possible with the process, are not confined to the particular membrane process, but apply to any workable water removal process.

SUMMARY OF THE INVENTION

In work leading to the present invention, it has now been found that it is possible to use a suitable semi-permeable membrane to remove water and possibly other reaction product(s), including urea, from the reaction mixture derived either from ammonia and carbon dioxide or from ammonium carbamate. Accordingly, the process of the present invention provides an improvement in the conversion of the starting materials to urea and/or in the rate of conversion of those materials to urea.

According to the present invention, there is provided a process for the production of urea which comprises the steps of reacting carbon dioxide and ammonia to form ammonium carbamate and subsequent decomposition of ammonium carbamate to form a reaction mixture comprising urea and water, wherein the reaction mixture is contacted with one side of a semi-permeable membrane, and a drying fluid capable of removing water and possibly other reaction product(s) from the reaction mixture is contacted with the other side of the semi-permeable membrane.

The ammonium carbamate may be formed in situ by reaction of ammonia and carbon dioxide in a synthesis/-conversion enhancement zone in contact with the semi-permeable membrane. Alternatively, the ammonium carbamate may be formed in a separate urea reactor as a synthesis zone, and the reaction mixture then passed to a conversion enhancement zone in contact with the membrane. In either case, an ammonium carbamate recycle mixture may, if desired, also be admitted to the synthesis zone together with ammonia and carbon dioxide in order to further improve the efficiency of conversion. The ammonia and carbon dioxide are used in a molar ratio known in the production of urea, typically a ratio of ammonia to carbon dioxide of greater than 2.

The reaction may, for example, be carried out at a temperature in the range of 140° to 250° C., preferably 160° to 220° C., and at a pressure in the range of 15 to 50 MPa, preferably 25 to 45 MPa.

It will be understood that the semi-permeable membrane must be made of a material which can withstand the high temperature and pressure conditions involved in the urea synthesis process. In one embodiment of this process, the temperature or pressure may be adjusted so as to be at least substantially the same on the two sides of the membrane. Alternatively, however, the temperature and/or pressure may be different on the two sides of the membrane, provided that the membrane is sufficiently strong or sufficiently supported to withstand the pressure differential. The membrane must also have a higher permeability for the transport of water and possibly also urea than for the other components of the reaction mixture, particularly carbon dioxide and ammonium carbamate. Suitable materials are described in detail hereinafter.

The drying fluid used in accordance with this invention may be any fluid which can cause water and possibly other reaction product(s), including urea, in the reaction mixture to preferentially migrate across the membrane. Ammonia is the presently preferred drying fluid. In its supercritical state (above 132° C. and 12 MPa), ammonia forms a dense fluid having a high affinity for water and dissolves urea. It will, however be understood that other drying fluids such as air or carbon dioxide may also be used in accordance with the invention.

The present invention differs from a conventional reverse osmosis process (suggested in the Ruf et al papers referred to above) in the use of a drying fluid as described herein on the other side of the membrane to the reaction mixture, and may, for example, be carried out with the pressure substantially equal on both sides of the membrane.

In general terms, the present invention includes a process for production of urea (carried out in either one or two stages) wherein carbon dioxide, ammonia, and/or ammonium carbamate is reacted in a synthesis zone, and if necessary the reaction mixture is transfered from the synthesis zone into a conversion enhancement zone, which includes:

(a) utilizing a semi-permeable membrane, which has a higher permeability for the transport of water and possibly also urea, than for the other components of the reaction mixture, particularly than for carbon dioxide or ammonium carbamate, in the conversion enhancement zone, with the said semi-permeable membrane being suitably held and supported;

(b) feeding the reaction mixture to one side of the said semi-permeable membrane at a suitable high temperature and pressure;

(c) feeding a drying fluid such as ammonia to the other side of the said semi-permeable membrane at a suitable temperature and pressure;

(d) removing a portion of the enhanced reaction mixture, containing a lesser percentage of carbon in the form of carbon dioxide and ammonium carbamate combined (and usually a higher percentage of urea) than in the said reaction mixture, (e) recovering urea from the removed portion of the enhanced reaction mixture, and if desired, (f) recovering urea from the drying fluid.

The semi-permeable membrane used in the process of the present invention can be made from any membrane material which has the required properties and is sufficiently stable under the temperature and pressure conditions of the process. For example, such a material can be a perfluorocarboxylate membrane (such as FLEMION), a perfluorosulphonate membrane (such as NAFION 117), a reinforced version of such a membrane (for example NAFION 423 or NAFION 324) or a combination of these types of structure (such as NAFION 901). Alternatively, another material or a composite material such as one combining one or more materials, for instance polymers, with other types of materials, for example a porous ceramic membrane material, may be used to achieve improved conversion and/or stability. The said semi-permeable membrane can be in any convenient form, such as for example in the form of film, as a sheet or in the form of hollow fibres or of tubes, as is well known to those skilled in the technology of membranes. (FLEMION is the registered trade mark of Asahi Glass Co. Ltd., Japan; NAFION is the registered trade mark of E. I. DuPont de Nemours & Co., U.S.A.)

In tests conducted to date, it has been established that the process of the present invention is capable of achieving a higher conversion to urea in a single pass through the process than any previously reported urea synthesis process. In addition, the present invention enables a speeding-up of the urea conversion process.

Further details of the present invention will now be described by way of example, with reference to the accompanying drawings.

BRIEF DESCRIPTION OF DRAWINGS

FIG. 2. depicts schematically another apparatus for carrying out the process of the invention and which utilizes an internal conversion enhancement zone (Internal CEZ);

FIG. 3. shows the glass reaction cell (GRC). referred to in Example 1.

DETAILED DESCRIPTION OF THE PROCESS OF THE INVENTION

Figure 1:
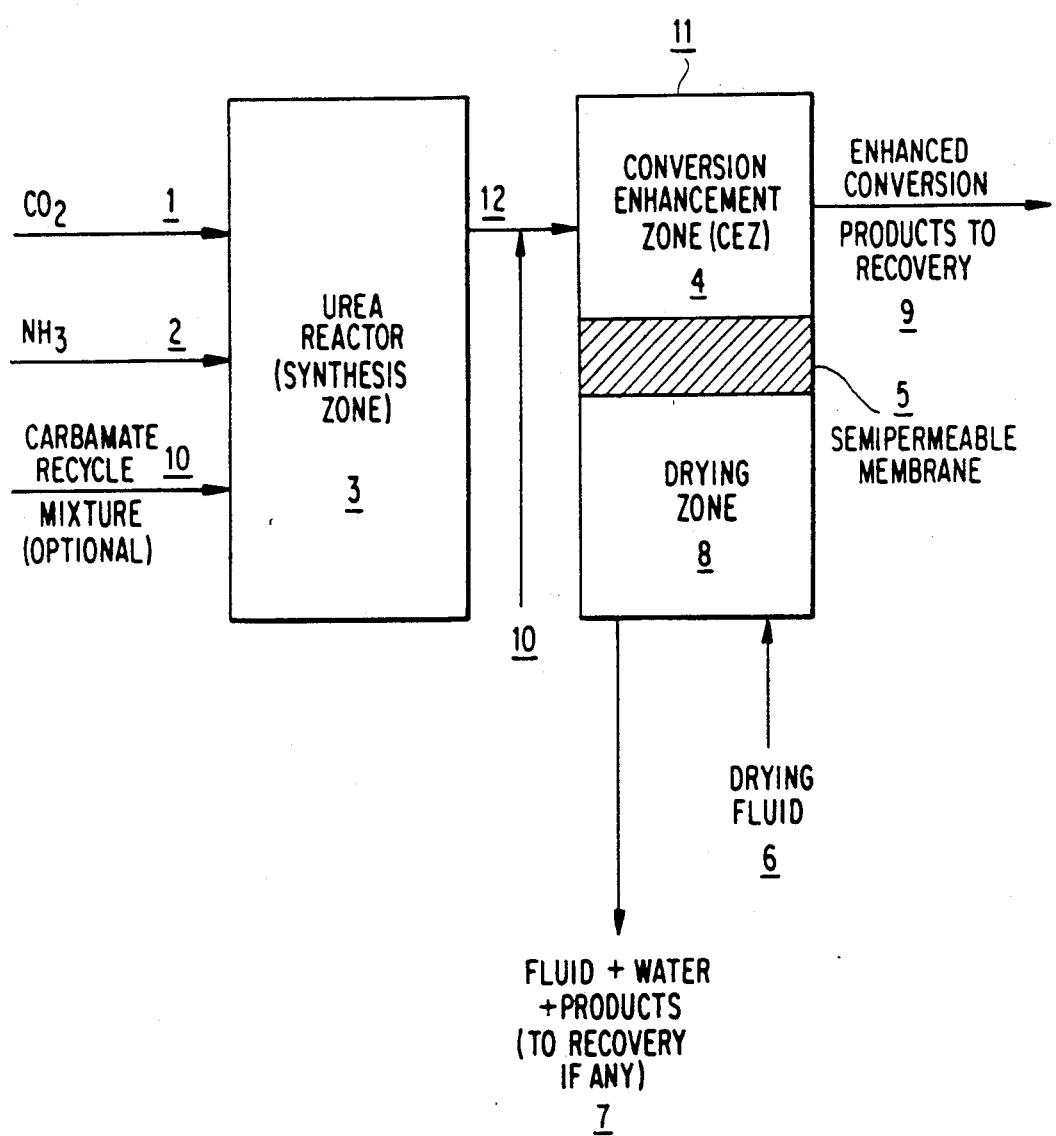
FIG. 1. depicts schematically one apparatus for carrying out the process of the invention and which utilizes an external conversion enhancement zone (External CEZ)

As described above, a feature of the process is the transfer of water and possibly other reaction product(s), including urea, from the conversion enhancement zone across a suitable semi-permeable membrane to a drying fluid to allow the forward reaction of carbamate to urea to be enhanced relative to the reverse reaction, thus increasing conversion. As previously described, the drying fluid can be any fluid which can cause water and possibly other reaction product(s) to preferentially migrate from the conversion enhancement zone across the membrane, for example ammonia.

The invention may, for example, be performed in either of two ways. The conversion enhancement zone (CEZ) can be either incorporated in the synthesis reactor (Internal CEZ), or it may be incorporated in a separate reactor following the synthesis reactor (External CEZ). Either of the two methods can be utilized in a new urea process plant. By retrofitting, the latter method (External CEZ) will be applicable to existing plants and the former method (Internal CEZ) may be applicable to existing plants in suitable cases depending on the existing process design.

The External CEZ embodiment, illustrated in the accompanying diagram of FIG. 1, which is applicable to the general case of retrofitted existing urea plants or to new plants, comprises a vessel 11 containing semi-permeable membrane(s) 5 located downstream of the urea reactor (synthesis zone) 3 and fed with reaction mixture 12. Simultaneously, a drying fluid 6 is fed to the drying zone 8 which is on the opposite side of the semi-permeable membrane 5. There is a preferential transference of water and possibly other reaction product(s) from the fluid in the conversion enhancement zone 4 to the fluid in the drying zone 8 across the semi-permeable membrane 5 thus causing further reaction of carbamate to urea in the conversion enhancement zone 4. As a further option, carbamate recycle mixture 10 may be fed additionally to the synthesis zone 3 and/or the CEZ 4. An enhanced reaction mixture 9 is removed from the CEZ 4, and urea is recovered from the enhanced reaction mixture 9, and optionally from the fluids 7 removed from the drying zone 8.

The Internal CEZ embodiment shown schematically in FIG. 2, is applicable in the case of new urea plants and those existing urea plants with suitable reactors. The membrane(s) 5 is (are) incorporated into the primary reactor 13 which includes the synthesis zone 3 and the CEZ 4. In accordance with common practice, carbon dioxide 1 and ammonia 2 are fed to the urea reactor for reaction first to carbamate then to urea in the synthesis zone 3. As an option, carbamate recycle mixture 10 may also be fed additionally to the synthesis zone 3. There is a preferential transference of water and possibly other reaction product(s) from the conversion enhancement zone (CEZ) 4 across the membrane 5 to the drying fluid 6 fed to the drying zone 8, thus causing further reaction of carbamate to urea in the CEZ 4. An enhanced reaction mixture 9 is removed from the CEZ 4, and urea is recovered from the enhanced reaction mixture 9, and optionally from the fluids 7 removed from the drying zone 8.

The following example of the invention are not intended to be limiting in nature, but illustrate the improved conversion which may be obtained in accordance with this invention.

EXAMPLE 1

(a) Apparatus:

The apparatus used in this Example is illustrated in FIG. 3. As shown, a glass reaction cell 14 (GRC) consists of two halves 15, 16 (each of 9.3 cm$^3$ volume) separated by a semi-permeable membrane of NAFION 117 (a perfluorosulphonate membrane) 17 (in the first experiment only) and teflon gaskets 18. The experiments were conducted under a pressure of anhydrous ammonia in a stainless steel autoclave with a glass liner. The pressure was transmitted to both halves of the GRC by glass capillaries 19, 20 (each 1 mm ID.). The capillaries served to prevent loss of the reagents from the GRC during the period of the reaction.

(b) Preparation of Ammonium Carbamate:

Ammonium carbamate was prepared by passing dry carbon dioxide gas into anhydrous liquid ammonia in a glass apparatus, removing excess ammonia and carbon dioxide in a vacuum desiccator, and storing the dry carbamate in sealed glass ampoules prior to use.

(c) Analytical Method for Urea:

The products of the experiments were collected and analysed for urea gravimetrically by allowing most of the excess ammonia to evaporate, dissolving the products in water (100 to 300 cm$^3$) and drying in a rotary evaporator under vacuum at 85°±3° C. The gravimetric method was tested on mixtures of carbamate and urea over the whole range of concentrations and found accurate to better than ±0.5%. Elemental analysis of the carbamate and of recovered urea showed that C,H,N and O were in both cases in the correct proportions within the accuracy of the analysis of ±0.4%.

(d) Reaction With the Semi-permeable Membrane:

In the first experiment, 4.3 g ammonium carbamate was loaded into the upper half 15 of the GRC above the membrane 17. The reaction was conducted for one hour at a temperature of 175°±2° C. under a pressure of anhydrous ammonia of 40±3 MPa.

(e) Reaction Without the Membrane:

In the second experiment, the membrane was omitted and 4.4 g ammonium carbamate was loaded into the lower half 16 of the GRC. The reaction was conducted for one hour at a temperature of 175°±2° C. under a pressure of anhydrous ammonia of 40±3 MPa.

(f) Results:

The conversion of carbamate to urea in the experiment with the membrane was 86.8%. The conversion of carbamate to urea in the experiment without the membrane was 74.1%.

This Example demonstrates conversion of ammonium carbamate to urea in the CEZ in either of the two ways of use of the invention: either the External CEZ as in FIG. 1. or the Internal CEZ as in FIG. 2, with a residence time of the order of 1 hour under the conditions of the experiment, with the upper half GRC 15 acting as the CEZ 4 and the lower half GRC 16 acting as the drying zone 8 (see FIG. 1 and FIG. 2). This Example further demonstrates a higher conversion in a single pass under the given conditions by use of the invention than any previously reported.

EXAMPLE 2

Experiments were conducted in the same apparatus and following the same procedures as in Example 1, with the exception that the membrane used was NAFION 423, and the reaction was conducted for one hour at 165°±2° C. (both with and without the membrane).

The conversion of carbamate to urea in the experiment with the membrane was 68.6%. The conversion of carbamate to urea in the experiment without the membrane was 54.8%.

EXAMPLE 3

The same procedures and apparatus as in Example 2 were used in further experiments, with the exception that the reactions with and without the membrane were conducted for two hours at 165°±2° C.

The conversion of carbamate to urea in the experiment with the membrane was 79.1%, while the conversion in the experiment without the membrane was 69.0%.

EXAMPLE 4

The same procedures and apparatus as in Example 2 were used in further experiments, with the exception that the reactions with and without the membrane were conducted for three hours at 165°±2° C.

The conversion of carbamate to urea in the experiment with the membrane was 86.1%, while the conversion in the experiment without the membrane was 71.3%.

EXAMPLE 5

The same procedures and apparatus as in Example 2 were used in further experiments, with the exception that the membrane used was NAFION 324.

The conversion of carbamate to urea in the experiment with the membrane was 76.8%, while the conversion in the experiment without the membrane was 54.8%.

EXAMPLE 6

The same procedures and apparatus as in Example 5 were used in further experiments, with the exception that the reactions with and without the membrane were conducted for six hours at 165°±2° C.

The conversion of carbamate to urea in the experiment with the membrane was 92.8%, while the conversion in the experiment without the membrane was 86.2%.

EXAMPLE 7

The same procedures and apparatus as in Example 1 were used in further experiments, with the exception that the reactions with and without the membrane were conducted under a pressure of anhydrous ammonia of 29±3 MPa.

The conversion of carbamate to urea in the experiment with the membrane was 79.7%, while the conversion in the experiment without the membrane was 68.1%.

EXAMPLE 8

The same procedures and apparatus as in example 2 were used in further experiments, with the exception that the membrane used was NAFION 901.

The conversion of carbamate to urea in the experiment with the membrane was 61.6%, while the conversion in the experiment without the membrane was 54.8%.

EXAMPLE 9

The same procedure and apparatus as in Example 2 were used in further experiments, with the exception that the temperature used was 180°±2° C.

The conversion of carbamate to urea in the experiment with the membrane was 86.9%, while the conversion in the experiment without the membrane was 77.7%.

Examples 1 to 9 show that a higher conversion of carbamate to urea is achieved in a given time with the membrane and drying fluid in accordance with this invention, than without the membrane. In addition, a comparison of Examples 3 and 4, by way of example, shows that conversion of carbamate to urea in two hours in accordance with the invention in Example 3 is greater than in three hours without the membrane in Example 4 under otherwise identical conditions. This demonstrates that the rate of conversion is increased in accordance with the invention.

It will be understood by persons skilled in this art that modifications or variations may be made to the particular embodiment described in detail herein without departing from the broad principles of the invention as described above, and that the ambit of the present invention extends to encompass all such modifications and variations.

We claim:

1. A process for the production of urea which comprises the steps of reacting carbon dioxide and ammonia to form ammonium carbamate and subsequent decomposition of ammonium carbamate to form a reaction mixture comprising urea and water, wherein the reaction mixture is contacted with one side of a semi-permeable membrane, a drying fluid capable of removing water and possibly other reaction product(s) from the reaction mixture is contacted with the other side of the semi-permeable membrane, and urea is recovered from the reaction mixture after contact with the semi-permeable membrane and optionally also from the drying fluid.

2. A process for the production of urea which comprises the steps of reacting carbon dioxide and ammonia to form ammonium carbamate and subsequent decomposition of ammonium carbamate to form a reaction mixture comprising urea and water, wherein the reaction mixture is contacted with one side of a semi-permeable membrane, a drying fluid capable of removing water and possibly other reaction product(s) from the reaction mixture is contacted with the other side of the semi-permeable membrane, and urea is recovered from the reaction mixture after contact with the semi-permeable membrane and optionally also-from the drying fluid, and wherein the ammonium carbamate is formed and decomposed to form said reaction mixture comprising urea and water in a combined synthesis/conversion enhancement zone in contact with said semi-permeable membrane.

3. A process for the production of urea which comprises the steps of reacting carbon dioxide and ammonia to form ammonium carbamate and subsequent decomposition of ammonium carbamate to form a reaction mixture comprising urea and water, wherein the reaction mixture is contacted with one side of a semi-permeable membrane, a drying fluid capable of removing water and possibly other reaction product(s) from the reaction mixture is contacted with the other side of the semi-permeable membrane, and urea is recovered from the reaction mixture after contact with the semi-permeable membrane and optionally also from the drying fluid, and wherein the ammonium carbamate is formed and decomposed to form said reaction mixture comprising urea and water in a synthesis zone, and said reaction mixture is then passed to a separate conversion enhancement zone in contact with said semi-permeable membrane.

4. A process according to claim 2 or claim 3 wherein an ammonium carbamate-containing recycle mixture is admitted to the synthesis zone together with said ammonia and carbon dioxide.

5. A process according to any one of claims 1 2 or 3, wherein said semi-permeable membrane has a higher permeability for the transport of water, and possibly also urea, than for the other components of said reaction mixture.

6. A process according to claim 5, wherein said semi-permeable membrane is an optionally reinforced material selected from perfluorocarboxylate and perfluorosulphonate membrane materials, or a combination thereof.

7. A process according to any one of claims 1 2 or 3, wherein said drying fluid is a fluid which can cause water and possibly other reaction product(s) in said reaction mixture to preferentially migrate across said semi-permeable membrane.

8. A process according to claim 7, wherein said drying fluid is ammonia.

9. A process according to any one of claims 1 2 or 3, wherein said reaction is performed at a temperature in the range of 140° to 250° C.

10. A process according to any one of claims 1 2 or 3, wherein said reaction is performed at a pressure in the range of 15 to 50 MPa.

11. A process according to any one of claims 1 2 or 3, wherein the temperature and/or pressure are adjusted to be substantially the same on both sides of said semi-permeable membrane.

12. A process according to any one of claims 1 2 or 3, wherein the temperature and/or pressure are different on the two sides of the semi-permeable membrane.

13. A process according to any one of claims 1 2 or 3, wherein:
a) said reaction mixture is formed at or fed to one side of said semi-permeable membrane;
b) said drying fluid is fed to the other side of said semi-permeable membrane;
c) an enhanced reaction mixture containing a lower percentage of carbon in the form of carbon dioxide and ammonium carbamate than in the said reaction mixture is removed; and
d) urea is recovered from said enhanced reaction mixture, and optionally from said drying fluid.

14. A process according to claim 9 wherein said reaction is performed at a temperature in the range of 160° to 220° C.

15. A process according to claim 10 wherein said reaction is performed at a pressure in the range of 25 to 45 MPa.

* * * * *